United States Patent
Lee

(10) Patent No.: US 6,616,636 B2
(45) Date of Patent: Sep. 9, 2003

(54) DISPOSABLE SAFETY SYRINGE WHICH LEAVES NO RESIDUAL INJECTION

(76) Inventor: Choon-Bal Lee, Gicheung-101, Dongheung Villa, 787-4, Kyesan-dong, Keyang-ku, Incheon-shi (KR)

( * ) Notice: Subject to any disclaimer, the term of this patent is extended or adjusted under 35 U.S.C. 154(b) by 0 days.

(21) Appl. No.: 09/817,848

(22) Filed: Mar. 26, 2001

(65) Prior Publication Data

US 2002/0107489 A1 Aug. 8, 2002

(30) Foreign Application Priority Data

Feb. 3, 2001 (KR) ........................... 2001-2603 U

(51) Int. Cl.[7] ............................... A61M 5/32; A61M 5/00
(52) U.S. Cl. ........................................ 604/192; 604/235
(58) Field of Search ............................... 604/110, 263, 604/192, 198, 164.08, 235, 162, 199; 206/570, 571, 364, 365

(56) References Cited

U.S. PATENT DOCUMENTS

| | | | | |
|---|---|---|---|---|
| 2,879,766 A | * | 3/1959 | Wilburn | |
| RE25,113 E | * | 1/1962 | Wilburn | |
| 3,485,239 A | * | 12/1969 | Vanderbeck | |
| 3,672,369 A | * | 6/1972 | Brown | 128/218 |
| 3,783,998 A | * | 1/1974 | Brush et al. | 206/43 |
| 3,893,608 A | * | 7/1975 | Koenig | 225/1 |
| 4,233,975 A | * | 11/1980 | Yerman | |
| 4,237,882 A | * | 12/1980 | Wickham | 128/218 |
| 4,300,678 A | * | 11/1981 | Gyure et al. | 206/364 |
| 4,367,738 A | * | 1/1983 | Legendre et al. | 128/218 |
| 4,713,060 A | * | 12/1987 | Ruili | 604/199 |
| 4,743,233 A | * | 5/1988 | Schneider | 604/192 |
| 4,801,295 A | * | 1/1989 | Spencer | 604/198 |
| 4,840,619 A | * | 6/1989 | Hughes | 604/240 |
| 4,878,903 A | * | 11/1989 | Mueller | 604/199 |
| 4,929,232 A | * | 5/1990 | Sweeney et al. | 604/111 |
| 4,932,941 A | * | 6/1990 | Min et al. | 604/110 |
| 4,968,304 A | * | 11/1990 | Alter et al. | 604/192 |
| 5,053,018 A | * | 10/1991 | Talonn et al. | 604/198 |
| 5,112,316 A | * | 5/1992 | Venturini | 604/195 |
| 5,147,328 A | * | 9/1992 | Dragosits et al. | 604/218 |
| 5,158,550 A | * | 10/1992 | Scholl, Jr. | 604/110 |
| 5,342,323 A | * | 8/1994 | Haining | 604/195 |
| 5,496,285 A | * | 3/1996 | Schumacher et al. | 604/218 |
| 5,902,270 A | * | 5/1999 | Jentzen | 604/110 |
| 6,053,894 A | * | 4/2000 | Shadd, Jr. | 604/191 |

* cited by examiner

*Primary Examiner*—Sharon Kennedy
(74) *Attorney, Agent, or Firm*—Howrey Simon Arnold & White

(57) ABSTRACT

The present invention relates to a disposable safety syringe constructed such that the attached needle may be disposed of safely after use, and additionally configured so that all fluid is forced from the barrel of the syringe, and further constructed so that the plunger may not be fully removed from the barrel, preventing the inadvertent loss of fluid that has been drawn into the syringe barrel.

18 Claims, 5 Drawing Sheets

DISPOSABLE SAFETY SYRINGE WHICH LEAVES NO RESIDUAL INJECTION

CROSS REFERENCE TO RELATED APPLICATION

This application claims priority under 35 U.S.C. §119(a) to Korean Utility Model Application No. 2603/2001, filed in Korea on Feb. 3, 2001.

TECHNICAL FIELD

The present invention is directed to a disposable safety syringe constructed so that an attached needle may be disposed of safely and separately after use, additionally configured so that all fluid is forced from the barrel of the syringe, and further constructed so that the plunger may not be fully removed from the barrel, preventing inadvertent loss of fluid that has been drawn into the syringe barrel.

BACKGROUND OF THE INVENTION

A conventional disposable syringe is constructed such that fluid to be injected is forced out of the barrel of the syringe when pressure is exerted on the syringe plunger. The barrel of a conventional syringe typically tapers at one end to accommodate the base of a needle.

When the plunger is forced into the barrel, the end of the plunger cannot fully enter this tapered portion of the barrel. Thus, a small amount of the injection fluid is left unaffected by pressure exerted by the plunger, and remains in the tapered portion of the barrel. Although this remaining amount of fluid (e.g. 0.07 cc) may seem negligible, repeated waste of this small quantity leads to economic loss.

A conventional syringe also lacks a mechanism to prevent one from pulling the plunger completely out of the barrel. If one mistakenly removes the plunger while drawing fluid into the barrel, the fluid can be lost.

Conventional disposable needles are typically covered by a cap for protection. This cap is removed before use, and replaced prior to needle disposal. If this conventional needle cap inadvertently falls off, individuals handling the needle, such as health care professionals and sanitation workers, may be pricked by the exposed needle, potentially exposing themselves to blood borne diseases.

SUMMARY OF THE INVENTION

The present invention remedies the aforementioned problems by incorporating several novel features. First, a plunger tip of new design allows all fluid to be forced from the tapered portion of the syringe barrel into the needle. Second, a slanted protrusion on the interior of the barrel prevents a user form inadvertently pulling the plunger fully out of the barrel. Third, after an injection is given, a newly designed protective needle shield can be moved and locked into position, shielding the needle from touch. A disposal cap may then be placed on the top of this shield. The movement of this shield into position also allows dislocation of the protected shield and needle from the syringe, allowing for separate needle disposal.

DETAILED DESCRIPTION OF PREFERRED EMBODIMENTS

Figure 1:
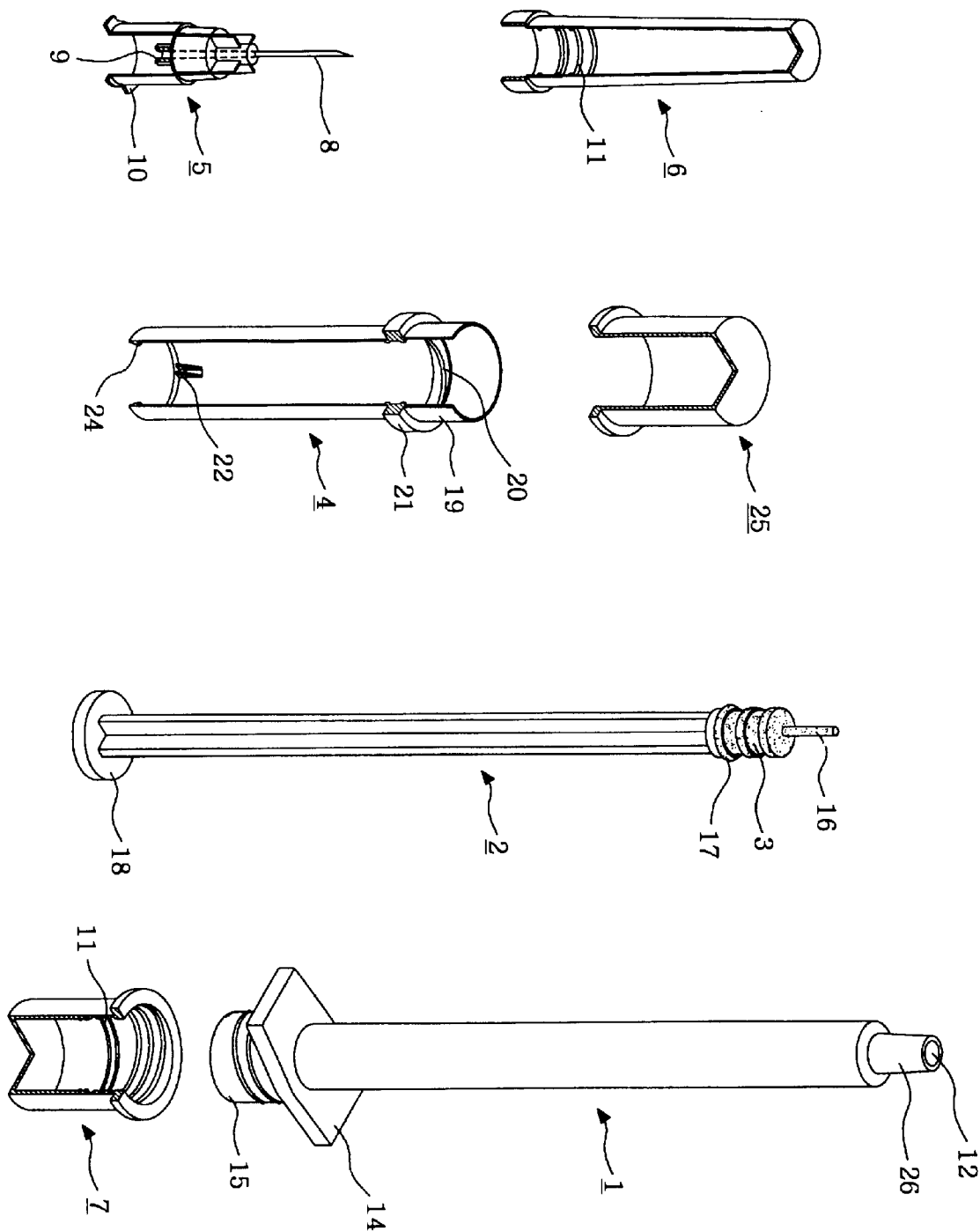
FIG. 1 shows the disassembled components of an embodiment of the disclosed syringe and needle, as well as the various protective caps.

Referring to FIG. 1, in one embodiment of the invention, the syringe barrel 1 has a first end and a second end. On the first end, there is a tapered portion of the barrel 26, upon which a needle base 5 containing a needle 8 can be placed. On the second end of the barrel there is a finger flange 14, where fingers may be placed during use to allow one to advance or withdraw a plunger 2 within the barrel 1. Also on the second end of the barrel, distal to the finger flange 14, is a rear cap receptacle 15. Threads on the exterior of the rear cap receptacle 15 correspond to threads located on the interior of a rear cap 7. This rear cap 7 can be disengagably connected to the barrel 1 of the syringe via the rear cap receptacle 15. One or more sterility rings 11, also located on the interior of the rear caps form an airtight seal with the rear cap receptacle 15.

Referring again to FIG. 1, the plunger 2 has a thumb rest 18 at one end, and an injection tip 3, upon which is mounted an injection tip protrusion 16, at the other.

Figure 2:
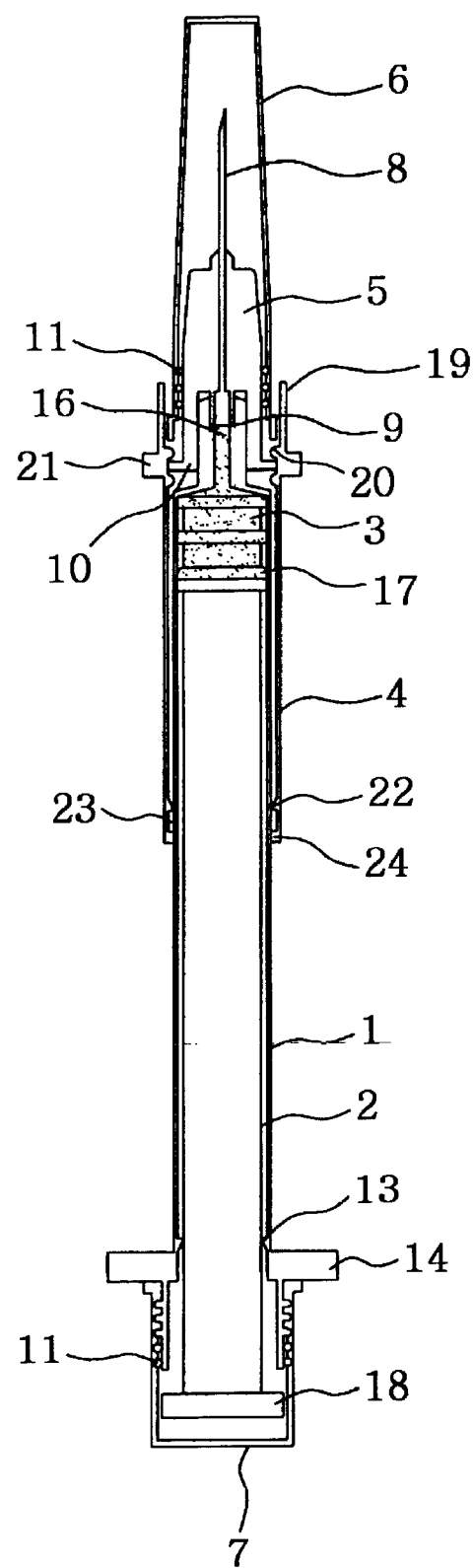
FIG. 2 is a cross-sectional view of an embodiment of the assembled syringe and needle with end caps, as it would appear prior to use.
Figure 3:
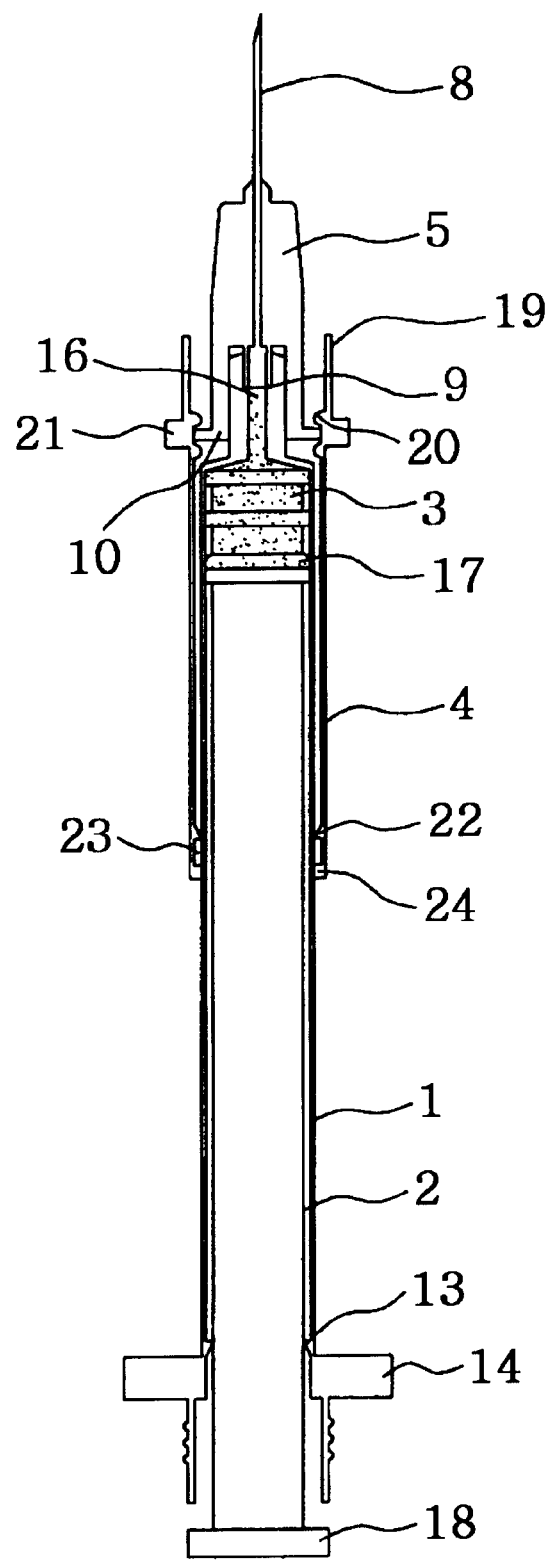
FIG. 3 is a cross-sectional view of an embodiment of the syringe with attached needle after the needle cap and rear cap have been removed, wherein the plunger has been fully driven into the syringe barrel.
Figure 4:
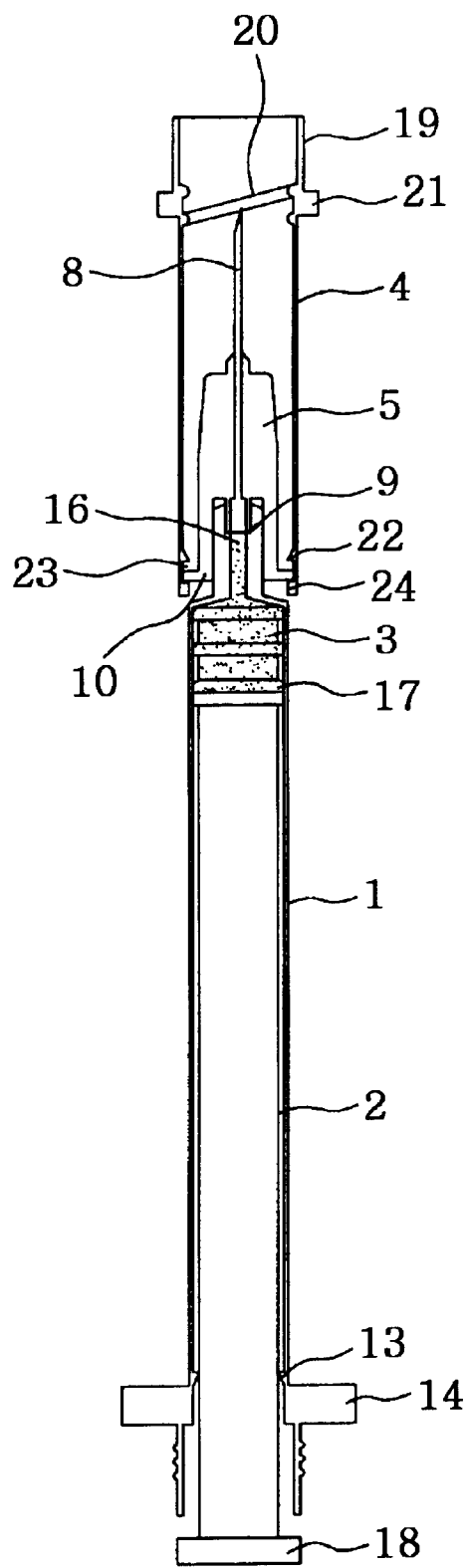
FIG. 4 is a cross-sectional view of an embodiment of the syringe with attached needle after the protective needle shield has been raised and locked into position, and the disposal cap has been placed on the protective needle shield.

Referring to FIGS. 2–4, the injection tip 3 is also encircled by one or plunger stopping ribs 17. These ribs 17 prevent a user from pulling the plunger 2 completely out of the barrel 1 by catching on slanted plunger stopping protrusions 13 located on the interior of the barrel 1. The inability to remove the plunger 2 completely from the barrel 1 assures that no fluid is inadvertently lost while attempting to draw it into the barrel.

In the assembled invention, a plunger 2 is contained within the syringe barrel 1. When the plunger 2 is forced into the barrel 1 completely, all fluid in the both the barrel 1 and the tapered portion of the barrel 26 is forced through the barrel outlet 12. Fluid is forced from the tapered portion of the barrel 26 by the injection tip protrusion 16, which is capable of entering the tapered portion of the barrel 26. This injection tip protrusion 16 will advance until it comes into contact with the back of the needle 9.

Additionally, in the assembled invention, a protective needle shield 4 surrounds the syringe barrel 1 and needle base 5. This needle shield 4 holds the needle base 5 in place atop the tapered portion of the barrel 26. A thread 20 on the interior of the needle shield 4 holds needle base protrusions 10 located at the bottom of the needle base 5.

Before use, a needle cap 6 shields the needle 8, and is held in place by contacts between one or more sterility rings 11 on the interior of the needle cap 6, with the exterior of the needle base 5.

When preparing to use the invention, the rear cap 7 and needle cap 6 are removed. After an injection is given, one may grasp and twist the needle shield 4 slightly by grasping the detachment handles 21. This action will disengage the needle base protrusions 10 at the bottom of the needle base 5 from the thread 20 on the interior of the needle shield 4.

As shown in FIG. 4, the needle protective shield 4 is then moved upwards to cover the exposed needle 8, and becomes locked into a shielding position when the needle base protrusions 10 glide over slanted protrusions 22, and are stopped by an adjacent catching ledge 24, both (22 and 24) located on the interior of the needle protective shield 4. The needle base protrusions 10 now rest in an indented space 23 between the slanted protrusions and the catching ledge 24, both on the interior of the shield 22.

At this time, the needle base 5, containing the used needle 8, is securely shielded by the needle protective shield 4, as the needle base protrusions 10 are now stuck in the indention 23 between the slanted protrusions 22 and the catching ledge 24. Thus, the use of the needle protective shield not only secures the needle for safety, but also prevents reuse of an unsanitary needle.

The movement of the needle shield 24 over the exposed needle 8 also allows one to disconnect the needle base 5 from the tapered portion of the barrel 26.

Once the needle protective shield reaches this shielding position, the needle can be further protected by placing a disposable cap 25 onto the disposal cap receptacle 19 of the needle protective shield 4, with the disposable cap 25 coming to rest on the detachment handles 21 at the base of the disposal cap receptacle 19.

Figure 5:
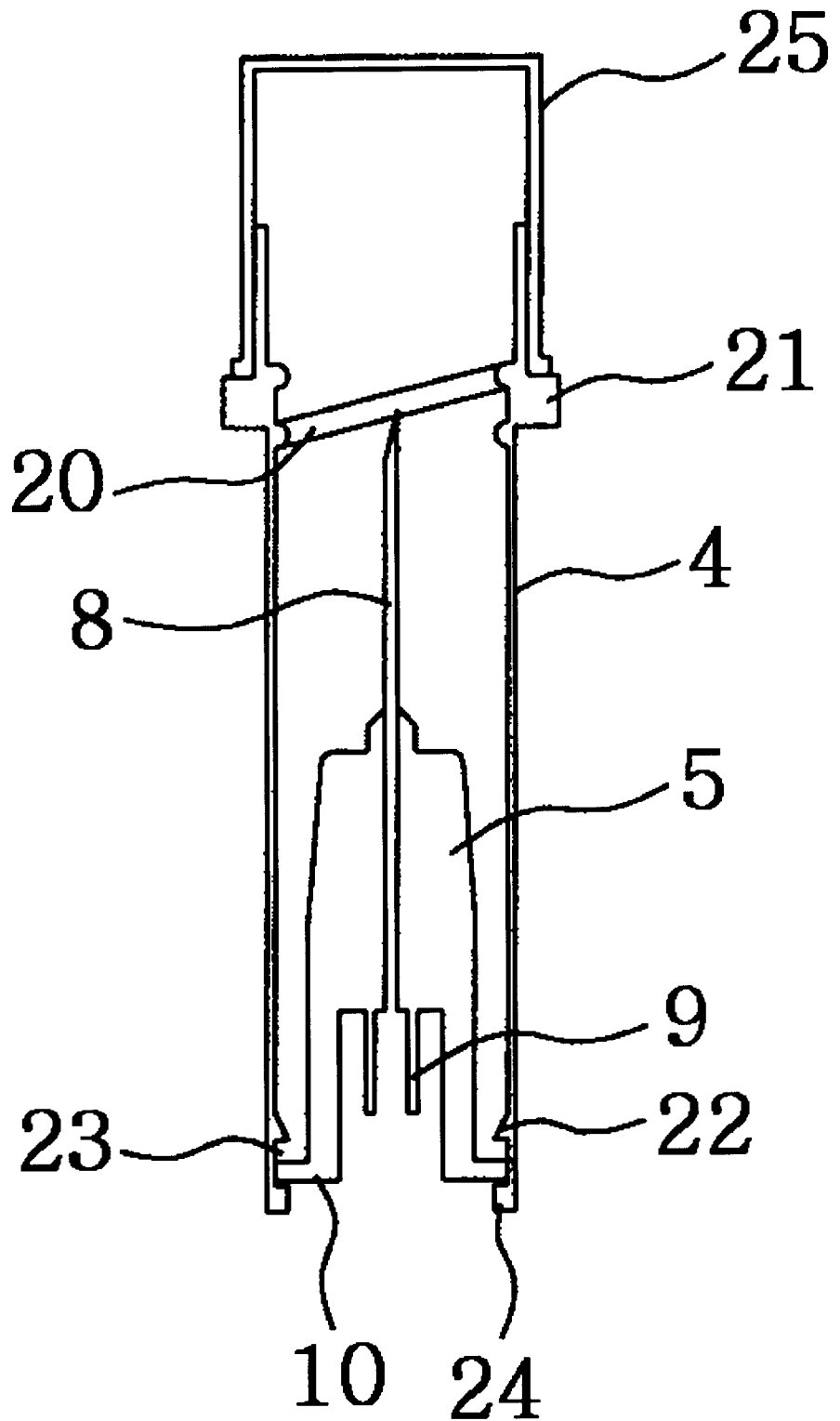
FIG. 5 is a cross-sectional view of the needle base, the protective needle shield, and the disposal cap after their removal from the syringe barrel.

As shown in FIG. 5, the combination of the needle base 5, needle protective shield 4, and disposable cap 25 may now be safely removed from the syringe barrel 1 and may be separately and appropriately discarded.

The syringe and attached needle, with rear cap 7 and needle cap 6 in place, can be sterilized by placing it inside a common sterilization chamber. The sterility maintenance rings 11 located on both the interior of the needle cap 6 and rear cap 7, serve in prolonging the sterility of the invention.

In summary, the present invention includes several novel features, all of which improve the safety and efficacy this disposable syringe and needle. First, by way of a newly designed plunger injection tip, all remnants of the injection fluid are forced from the barrel into the needle. Second, full removal of the plunger from the barrel is prevented by a combination of ribs surrounding the injection tip that catch on slanted protrusions located inside the syringe barrel. Third, a newly designed needle protective shield, which encircles the barrel and needle base may be moved into position after an injection is given, shielding the needle from touch, and also dislocating the needle protective shield and needle base from the syringe. A disposal cap may then be placed over the top of the needle protective shield, further preparing the shielded needle for appropriate disposal.

What is claimed is:

1. A disposable safety syringe, which leaves no residual injection, comprising:
   (a) a syringe barrel, which comprises a connecting tip for a needle base at an upper end of the syringe barrel; a barrel finger flange; a rear cap receptacle for maintaining sterility at a lower end of the syringe barrel; and a plunger stopping protrusion which is slanted toward the upper end of the syringe barrel around the inner diameter of the lower end of the syringe barrel;
   (b) a needle base connected to the connecting tip of the syringe barrel, wherein said needle base comprises a syringe needle connected to an upper end of the needle base; and a needle base protrusion at a lower end of the needle base;
   (c) a syringe plunger, which comprises an injection tip connected at an upper end of the plunger; a syringe thumb rest at a lower end of the plunger; an injection tip protrusion at an upper end of the injection tip; and a plunger stopping rib for contacting the plunger stopping protrusion to prevent loss of injection; and
   (d) a needle shield, placed outside of the syringe barrel, which comprises a disposable cap receptacle, and a detachment handle at an upper end of the needle shield.

2. The disposable safety syringe of claim 1, further comprising a rear cap for maintaining sterility connected to the rear cap receptacle.

3. The disposable safety syringe of claim 1, further comprising a disposable cap connected to the disposable cap receptacle.

4. The disposable safety syringe of claim 1, further comprising a protective cap connected to the needle base.

5. The disposable safety syringe of claim 2, further comprising multiple of sterility rings around an inside diameter of the rear cap.

6. The disposable safety syringe of claim 1, wherein the needle shield further comprises a thread for connecting the needle shield to the needle base; a slanted protrusion capable of passing over the needle base protrusion; and a catching ledge for catching the needle base protrusion and impeding its movement.

7. The disposable safety syringe of claim 4, further comprising multiple sterility rings around an inside diameter of the protective cap.

8. A disposable safety syringe comprising:
   (a) a syringe barrel having a tapered first end connectable to a needle base, and a second end;
   (b) a plunger within the syringe barrel having an injection tip protrusion capable of advancing into and forcing fluid out of the tapered end of the syringe barrel;
   (c) a rear cap receptacle on the second end of the syringe barrel capable of receiving a rear cap;
   (d) a needle connected to the needle base; and
   (e) a movable needle shield surrounding the syringe barrel, wherein the movable needle shield exposes the needle in a first position, and covers the needle in a second position.

9. The syringe of claim 8, wherein the tapered end defines a space and wherein the injection tip protrusion is capable of completely filling the space to force all of the liquid out of the tapered end.

10. The syringe of claim 8, further comprising a rear cap, wherein the rear cap contains at least one sterility ring for contacting a portion of the rear cap receptacle.

11. The syringe of claim 8, wherein the second end of the syringe barrel has on its interior at least one plunger stopping protrusion, wherein at least one of the plunger stopping protrusions is capable of contacting a portion of the plunger to prevent its removal from the syringe barrel.

12. The syringe of claim 8, wherein the needle shield further comprises a disposal cap receptacle capable of receiving a disposal cap when in the second position.

13. A disposable safety syringe, comprising:
   (a) a syringe barrel, having first and second ends;
   (b) a needle base connected to the first end of the syringe barrel, said needle base having a needle and one or more needle base protrusions;
   (c) a movable needle shield surrounding the exterior of the syringe barrel, wherein the needle shield has a thread at a first end and exposes the needle in a first position, wherein the movable needle shield is locked in the first position when the needle base protrusions and the movable needle shield thread are fixed in a screw relationship, and covers the needle in a second position, wherein the movable needle shield can be disengaged from the needle base protrusions by rotating the movable shield to be moved from the first to the second position, and wherein the needle shield is in contact with the needle base at both positions.

14. The syringe of claim 13, wherein needle base has at least one needle base protrusion, and wherein the needle shield has at least one indention at a second end, and wherein the needle shield is locked in the second position when at least one needle base protrusion meets with at least one needle shield indention.

15. The syringe of claim 13, wherein the first end of the syringe barrel is tapered, and further comprising a plunger within the syringe barrel, the plunger having an injection tip protrusion capable of advancing into and forcing fluid out of the tapered end of the syringe barrel.

16. The syringe of claim 13, wherein the second end of the syringe barrel has on its interior at least one plunger stopping protrusion, wherein at least one of the plunger stopping protrusions is capable of contacting a portion of a plunger in the syringe barrel to prevent its removal from the syringe barrel.

17. The syringe of claim 13, further comprising a rear cap receptacle on the second end of the syringe barrel and capable of receiving a rear cap.

18. The syringe of claim 17, further comprising a rear cap, which contains at least one sterility ring for contacting a portion of the rear cap receptacle.

* * * * *